United States Patent [19]

Papadakis

[11] Patent Number: 4,534,356
[45] Date of Patent: Aug. 13, 1985

[54] SOLID STATE TRANSCUTANEOUS BLOOD GAS SENSORS

[75] Inventor: Nicholas Papadakis, Mentor, Ohio

[73] Assignee: Diamond Shamrock Chemicals Company, Dallas, Tex.

[21] Appl. No.: 403,808

[22] Filed: Jul. 30, 1982

[51] Int. Cl.³ .............................................. A61B 5/00
[52] U.S. Cl. .................... 128/635; 204/403; 204/415; 204/431
[58] Field of Search ............... 128/635; 204/403, 415, 204/433, 431

[56] References Cited

U.S. PATENT DOCUMENTS

| | | | |
|---|---|---|---|
| 3,763,850 | 10/1973 | Gaudebout et al. | 128/635 |
| 3,912,614 | 10/1975 | Spracklen et al. | 204/403 X |
| 3,985,633 | 10/1976 | Lubbers et al. | 204/195 P |
| 4,120,770 | 10/1978 | Kessler | 204/195 P |
| 4,133,735 | 1/1979 | Afromowitz et al. | 204/433 X |
| 4,259,963 | 4/1981 | Huch | 128/635 |
| 4,265,250 | 5/1981 | Parker | 128/635 |
| 4,269,684 | 5/1981 | Zick | 204/195 R |
| 4,273,636 | 6/1981 | Shimada et al. | 128/635 X |
| 4,276,144 | 6/1981 | Hahn et al. | 204/195 P |
| 4,290,431 | 9/1981 | Herber et al. | 128/635 |
| 4,296,752 | 10/1981 | Welsh et al. | 128/635 |
| 4,312,332 | 1/1982 | Zick | 128/635 |
| 4,324,256 | 4/1982 | Vesterager | 128/635 |
| 4,324,257 | 4/1982 | Albarda et al. | 128/635 |
| 4,340,457 | 7/1982 | Kater | 204/403 X |
| 4,409,980 | 10/1983 | Yano et al. | 128/635 |

FOREIGN PATENT DOCUMENTS

| | | |
|---|---|---|
| 2943958 | 5/1981 | Fed. Rep. of Germany ...... 128/635 |
| 101249 | 8/1980 | Japan . |
| 1581338 | 12/1980 | United Kingdom . |
| 2056689 | 3/1981 | United Kingdom . |
| 2066962 | 7/1981 | United Kingdom . |

Primary Examiner—Lee S. Cohen
Attorney, Agent, or Firm—William A. Skinner; Bruce E. Harang

[57] ABSTRACT

Disclosed is a solid state oxygen sensor utilizing a noble metal first electrode and a silver/silver halide reference electrode and an oxygen permeable polymeric membrane electrolyte. Also disclosed is a method of producing said sensor and a method of using said sensor.

15 Claims, 5 Drawing Figures

SOLID STATE TRANSCUTANEOUS BLOOD GAS SENSORS

BACKGROUND OF THE INVENTION

This invention relates to transcutaneous oxygen sensors used to measure the amount of oxygen diffusing through the skin of a living body. More specifically, this invention relates to solid state sensors which have a surface permeable to oxygen which is adapted to engage the skin of the body and which may or may not also include a heating means.

It is known in the medical art of non-invasive blood oxygen content monitoring and measurement to apply to the surface of the skin of a person whose blood oxygen content is to be monitored and measured, a probe having a barrier permeable to oxygen and having an electrolyte solution stored above said membrane. In such a device, often referred to as a Clark electrode, a small voltage is applied between two electrodes having a gap which is bridged by the electrolyte solution and the current flow between the electrodes resulting from the reduction of the oxygen gas dissolved in the electrolyte is measured. The magnitude of the current is directly proportional to the amount of oxygen escaping from the blood and through the skin at the region where the probe is applied.

Generally there are two major problem areas with the state of the art associated with this type of transcutaneous oxygen sensor. The first is the fact that these sensors all require the heating of the skin in the range of 43° to 45° C. over which the sensor is located so as to promote vasodilation of the local blood vessels thereby increasing the blood flow to the region of application and thus also increasing the amount of oxygen diffusing through the skin for sensing by the probe. The second problem is that the state of the art requires a reservoir of liquid electrolyte over the membrane in which are immersed the electrodes. Thus, the apparatus itself is not disposable in most cases but the permeable membrane is. However, because no air or other gas bubbles can be trapped between the electrodes and the membrane within the liquid electrolyte, changing of the membranes themselves is a tedious and exacting procedure. This in turn requires that the sensor then be recalibrated.

Examples of the state of the art of heating assemblies are, for example, U.S. Pat. No. 4,290,431 to Herber et al wherein a semiconductor heating device is utilized within the transcutaneous oxygen sensor. Of similar nature is U.S. Pat. No. 4,296,752 to Welsh et al wherein a heater adjacent the electrode assembly is incorporated within the main body of the transcutaneous oxygen sensor.

Examples of the state of the art of the membrane technology are, for example, the above-identified patent references and also U.S. Pat. No. 4,259,963 issued to Huch et al and British Patent No. 2,056,689A issued to Leist et al.

U.S. Pat. No. 4,276,144 of Hahn et al teaches the use of a polymeric gas permeable layer over the end of an electrode in a multi-electrode assembly. However, this reference does not teach how to use these materials in a transcutaneous blood oxygen sensor assembly.

An example of an apparatus for oxygen partial pressure measurement incorporating a transcutaneous blood oxygen sensor is, for example, U.S. Pat. No. 4,269,684 of Zick. This reference, however, uses the standard type electrodes and liquid electrolyte reservoir.

Thus, a need still exists for a transcutaneous blood oxygen sensor which is for practical purposes a solid state device, does not need a pool of liquid electrolyte, and whose membrane does not have to be changed and the whole unit recalibrated.

SUMMARY OF THE INVENTION

Broadly stated, the present invention relates to a solid state oxygen sensor comprising an electrically insulating substrate; a first electrode comprising a noble metal on said substrate; a second electrode comprising a silver/silver halide reference electrode on said substrate; an insulating dielectric layer on said substrate and electrodes characterized in that at least a portion of said electrodes remain exposed; an oxygen permeable polymeric membrane containing a bound liquid electrolyte over at least said exposed portion of said electrodes further characterized in that said exposed portions of said first and second electrodes have well defined surface areas. Also taught is a process for making the solid state oxygen sensors of the present invention.

DETAILED DESCRIPTION OF THE INVENTION

Figure 1:
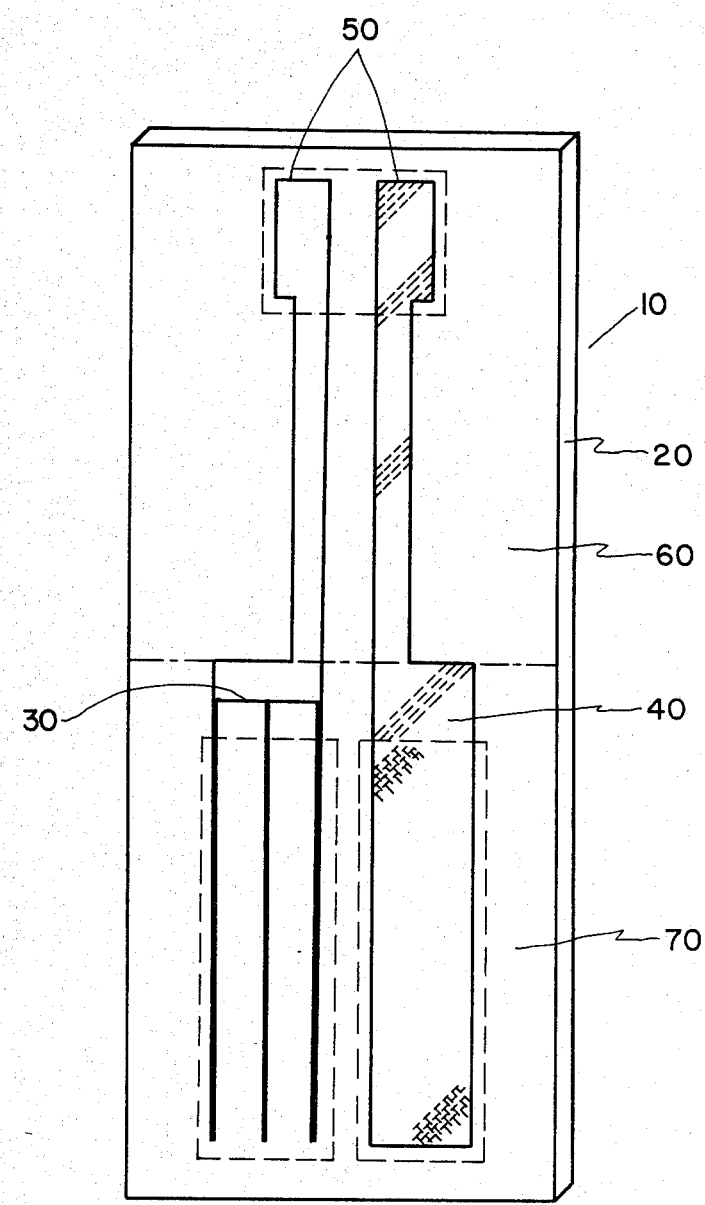
FIG. 1 is an enlarged perspective view of a transcutaneous oxygen blood gas sensor of the present invention.

The transcutaneous blood oxygen sensor of the present invention utilizes two electrodes in conjunction with one another. The first electrode is a noble metal. In the preferred embodiment, this electrode is made of gold or platinum metal. However, the other known noble metals are suitable for use in the present invention and include, for example, silver, palladium, iridium, rhodium, ruthenium, osmium and alloys thereof. It is to be understood, therefore, that the known alloys of noble metals are also encompassed by the use of the term "noble metal". The noble metal is generally deposited on the substrate utilizing thick film deposition techniques in conjunction with appropriate masks. This method produces well-defined surface areas which are needed for the polarographic oxygen measurement. Also of importance is the fact that these well-defined areas are reproducible to very close tolerances, sample to sample, allowing realization of a sensor that does not need to be calibrated by the user in most cases. These electrodes are most preferably formed using the appropriate masks (e.g. photo-resist) and metal slurries such as those supplied by, for example, Engelhard, E. I. duPont de Nemours, or Johnson Matthey. However, it will be appreciated that other methods (e.g. plasma sprayed thin films) and materials are suitable as long as a noble metal can be deposited on the selected substrate. In the most basic embodiment, this noble metal electrode is a single strip of noble metal. However, it is understood that more than one parallel strip of noble metal may be deposited and said strips electrically connected (also using noble metal) to produce the noble metal first electrode. This includes the use of the socalled "micro-electrode" concept. It is further understood that the necessary electrical contacts and connections on the sensors are also composed of a noble metal and/or alloy thereof as described hereinabove in conjunction with the first electrode hereinabove. Further, it is understood that the techniques used to fabricate the electrodes may also be used to fabricate the electrical contacts. Thus, the use of metal slurries and masks is a suitable technique. Also, these electrical contacts may be made before or after electrode formation, however, it is presently preferred to make them simultaneously with, and of the same material as, the electrode to which the contact is associated. Presently preferred is a first electrode composed of gold in three strips electrically connected such as shown in FIG. 1 number 30. A complete description of FIG. 1 shows that this sensor (10) comprises a substrate (20) a gold electrode (30) a silver/silver chloride reference electrode (40) an insulating material over some portion of the sensor (60) and a polymer electrolyte membrane containing a bound liquid electrolyte (70). Also shown are the electrical contacts (50) used to connect the sensor to the appropriate electrical device that will produce the polarization potential and record the response (the connections and electrical device are not shown).

The second electrode is a reference electrode comprising a silver/silver halide junction electrode. Suitable silver halides include, for example, silver chloride, silver bromide, silver iodide and silver fluoride. In the preferred embodiment, the silver halide of choice is silver chloride. The silver electrode is deposited on the substrate in a manner similar to that used for the first electrode as described hereinabove. Once the first and second electrodes have been deposited on the selected substrate, they are coated with a ceramic insulation material over the entire unit except areas, as for example, those enclosed by the dotted lines in FIG. 1. This ceramic insulation used in the preferred embodiment is a material supplied by Electro-Science Laboratories, Inc. This material is applied using thick film techniques utilizing a photo-resist and screening process as is well known in the thick film art. Additionally, thin film techniques such as, for example, plasma spraying may be used. The system utilized is not critical and is generally dictated by ease and cost factors. It should be noted that this ceramic insulation helps to define the exact electrode area used for the actual gas sensing or gas referencing as the case may be.

Once the above steps are completed, the silver electrode is halogenated by electrochemical techniques well-understood in that art. It is presently preferred to chloridate using a solution of 1% sodium chloride at 3.5 V with very low current flow for approximately 10 minutes.

Suitable substrates in the present invention include ceramic or glass chips, wafers, plates and other materials stable at the temperatures needed for the metal deposition. In the embodiment shown in FIG. 1, for example, the substrate is an alumina plate from the 3M Company. These substrates may be cut to desired size, as necessary, using known techniques in the art. They may also be made to a specific size in the manufacturing process using techniques that are well known in the arts associated with making these substrate materials. The important criteria for the substrates is that they are electrically insulating and can keep their integrity during the heating cycles needed to deposit the electrodes onto them.

Once electrode fabrication is complete, a polymer electrolyte membrane is cast over the exposed electrode section, but excluding the electrical contact areas of the device as indicated, for example, by the dash-dot line in FIG. 1, using in the preferred embodiment a p-HEMA and methanol solution, by dip coating. Other appropriate polymer solutions and other appropriate coating methods may be used as it is not critical to the sensor. It is understood, however, that the polymer used must be permeable to oxygen. The types of materials generally contemplated to be suitable are those known in the art as "hydrogels" and/or "hydrophilic polymers" and may be either copolymers or homopolymers.

Suitable copolymers may either be regular copolymers containing substantially no other material in their matrices, or they may be copolymers which contain monomers such as styrene and vinyl acetate, for example. In certain instances, this type of tailoring of the copolymers with monomers may enhance the desirable properties of the oxygen permeable polymeric membranes. Examples of suitable copolymers which, may or may not contain monomers, include, for example, N-vinyl pyrrolidone and glycidyl methacrylate.

Homopolymers may also be used in the present invention. It is to be understood, however, that when homopolymers are discussed, they include materials which can also be identified as "slightly cross-linked homopolymers." That is, they contain a relatively small amount of an impurity either intrinsic in the production of the monomer or added purposely to insure enough cross-linking so as to protect the homopolymer from slowly dissolving away. An example of this type of homopolymer which is slightly cross-linked is hydroxyethyl methacrylate (HEMA). In addition to the specific copolymers and homopolymers listed above, copolymers, with or without monomers, and homopolymers suitable in the present invention may be polymerized from the following monomers: hydroxyalkyl acrylates and hydroxyalkyl methacrylates, for example, hydroxyethyl acrylate, hydroxypropyl acrylate, and hydroxybutyl methacrylate; epoxy acrylates and epoxy methacrylates, such as, for example, glycidyl methacrylate; amino alkyl acrylates and amino alkyl methacrylates; N-vinyl compounds, such as, for example, N-vinyl pyrrolidone, N-vinyl carbazole, N-vinyl acetamide, and N-vinyl succinimide; amino styrenes; polyvinyl alcohols and polyvinyl amines, which must be made from suitable polymeric precursors; polyacrylamide and various substituted polyacrylamides; vinyl pyrridine; vinyl sulfonate and polyvinyl sulfate; vinylene carbonate; vinyl acetic acid, and vinyl crotonic acid; allyl amine and allyl alcohol; and vinyl glycidyl ethers. Processes and procedures for creating copolymers and/or homopolymers from the above monomers are well-known and understood in that particular art. These parameters are not critical to the instant invention with the caveats that the final copolymer and/or homopolymer is oxygen permeable and nontoxic for animal, including human, use. In one embodiment, the finished sensor is then stored dry and, before use, soaked in an appropriate electrolyte which increases the membrane conductivity necessary for oxygen measurement such as, for example, a saline solution. In an alternative embodiment, the sensor is saturated with an electrolyte solution and stored in that state using hermetically sealed containers until said sensor is needed for use.

It is also possible and in some cases advantageous to coat the whole finished sensor with the exception of the contact points with a material that is gas permeable, fluid impermeable and blood compatible. This would in effect create a system wherein the electrolyte would not contact the patient at all. Examples of these kinds of materials are, for example, TEFLON (a trademark of duPont), a polyphenylene oxide (PPO), polyethylene and polypropylene. It is also contemplated that in this configuration the sensor of the present invention may be used as an invasive type sensor.

The preferred embodiment of the present invention uses a saline solution as the electrolyte, preferably an 0.09 N (approximately 0.1 molar) saline solution because it is readily available in the health industry and also it is nonirritating to the skin area to which it will come in contact. The saline solutions used in the health fields are well-known and therefore need no further explanation here. Other suitable electrolytes may be used. Examples of these other suitable electrolytes include, for example, 0.1 M sodium chloride or 0.1 M potassium chloride solution utilizing a solvent comprising a 1:1 water:ethylene glycol mixture. Further, this electrolyte may be buffered to a pH range of 6-8 as is well-known in the art.

To ensure proper insulating, the electrical connectors indicated as number 50 in FIG. 1 are waterproofed, for example, silicone adhesive covered, before use or the physical configuration of the sensor is such that these contact points will not be exposed to the electrolyte solution. It is also understood that embodiments of the present invention having the electrical contacts on the face of the ceramic substrate opposite to the face having the electrodes will not need to be waterproofed to prevent exposure to the electrolyte.

It will be appreciated that the sensor must be connected to some type of electrical device that will produce the polarization potential of approximately 0.65 to 1.2 V preferably 1.15 V necessary to reduce the oxygen and allow for the recording of the response created by the oxygen across the two electrodes. The device is not shown in FIG. 1 and is contemplated to be any electric device capable of reading the current flow associated with this type of chemistry. These types of devices are well known and understood in the electrochemistry arts and therefore need no further elaboration here.

While in many cases the present invention does not need to have the patients' skin heated to be useful it may in some instances be helpful. Any known type of heating means which is capable of being regulated and able to hold the desired temperature in the range of 20° to 45° C. may be used. The heating means must, of course, be able to transmit its heat to the skin area immediately under and/or around the sensor of the present invention. Thus, it is presently contemplated that the heating means would be placed immediately on top of, and in contact with, the sensor of the present invention.

The following examples serve to illustrate the present invention without restricting it in any way.

EXAMPLE 1

A polargraphic oxygen ($PO_2$) sensor with two platinum (Pt) electrodes and one Ag/AgCl reference electrode was fabricated and in-vitro tested as follows:

All three electrodes were printed on a single alumina substrate (1"×1" 0.5 mm thick) from 3M, AlSiMag 772) using the thick film deposition method with platinum ink from Engelhard (A-3444) and silver ink from Electroscience Laboratories, Inc. (#9990). The Pt electrodes (dimensions: 2×23 mm and 6×23 mm) were deposited first and fired at the temperature recommended by the ink manufacturer, then the Ag electrode (6×23 mm) was formed again following the instructions of the ink manufacturer for high temperature firing. A ceramic dielectric coating (from Electroscience Laboratories, Inc. #4608) was printed on the top of the electrode side of the substrate using a photo-resist and screening technique such that only the contact points were exposed on the top of the chip and well-defined areas of the electrodes (2×15 mm, 6×15 mm and 6×13 mm) were formed at the lower part of the chip. The procedures for making masks via screening using a photo-resist material and using them for thick film depositions as described above are well-known in the electronic industry. The Ag/AgCl electrode was formed next electrochemically from a NaCl solution. The Ag surface was first etched in 1:1 $HNO_3$ solution for approximately 1 second then washed with distilled water and placed in a 1% NaCl solution across from a Pt screen. A polarization potential of 3.5 V was applied across the Ag (anode) and the Pt screen cathode with the current flow adjusted to 5.6 $mA/cm^2$. After 40 seconds, the polarization was reversed for 20 seconds (Ag cathodic) and then reversed again (Ag anodic) and maintained there for 10 minutes. This process gave reproducible and uniform AgCl coatings. The entire chip was immersed in distilled water after the chloridation step, for a period of 4 to 5 days, then dried in preparation for membrane coating.

A solution of p-HEMA (from Scientific Polymer Products cat. No. 414) was prepared by using a mixture (approximately 1:1) of tetrahydrofurfuryl alcohol and glycerol diacetate. The exact amount of p-HEMA in solution was not determined, but it was found that a 50 ml aliquot of this solution was enough to form a uniform film over the lower 65% to 70% area of the electrode side of the chip (area of interest including the exposed electrode surfaces and partially overlapping the insulation). The 50 ml aliquot of this solution was spread as uniformly as possible and then the chip (maintained flat) was placed in a vacuum oven (Fisher Model 231) and heated at 65° to 75° C. for 5.5 hours with a vacuum of approximately 15 inches of Hg.

Insulated wires (28 AWG) were soldered on the contact points using indium metal, and the entire area around the contact (not covered by the ceramic insulation) was coated with epoxy cement (DEVCON 5-minute epoxy).

The sample was now immersed in a solution of 0.1 M KCl, and 0.1 M $NaHCO_3$ in 1:1 water-ethylene glycol (by volume) for a total of 74 hours, then very quickly (to minimize water loss) mounted in the plexiglass test cell. The test cell had a total volume of approximately 4.35 $cm^3$ and provision for two (1"×1") chips to be mounted across from each other. Holes on the cell cover allowed for the insulated connection wires to pass through and were sealed (air tight) with a silicon adhesive (Dow Corning) after the sensor was mounted in the cell. During this experiment only the Ag/AgCl electrode and the larger Pt electrode (6×15 mm) were used. The gas inlet to the cell is located on the bottom, between the two sensor mounting areas and the outlet is on the top, such that the entire cell volume could be flushed on a continuous basis with the desired gas mixture. Both the gas inlet and outlet were connected to gas wash bottles, containing distilled water such that the humidity inside the cell could be maintained at a constant level. A flowmeter (AIRCO model S-75) was inserted in the gas inlet (before the wash bottle) in order to maintain a constant gas flow rate throughout the experiment, independent of the gas source. For this experiment, purified, compressed nitrogen gas and compressed air were used. The two gases were blended with an AIRCO model A-23 mixer such that the desired oxygen concentration was maintained in the test cell (oxygen content of compressed air was taken as 21%).

Nitrogen gas was allowed to flow through the cell for approximately 48 hours, before the polarographic data were collected. The test cell was not thermostated, but a thermocouple (Chromel-Alumel from OMEGA) located next to the sensor in the cell allowed continuous temperature monitoring.

Figure 2:
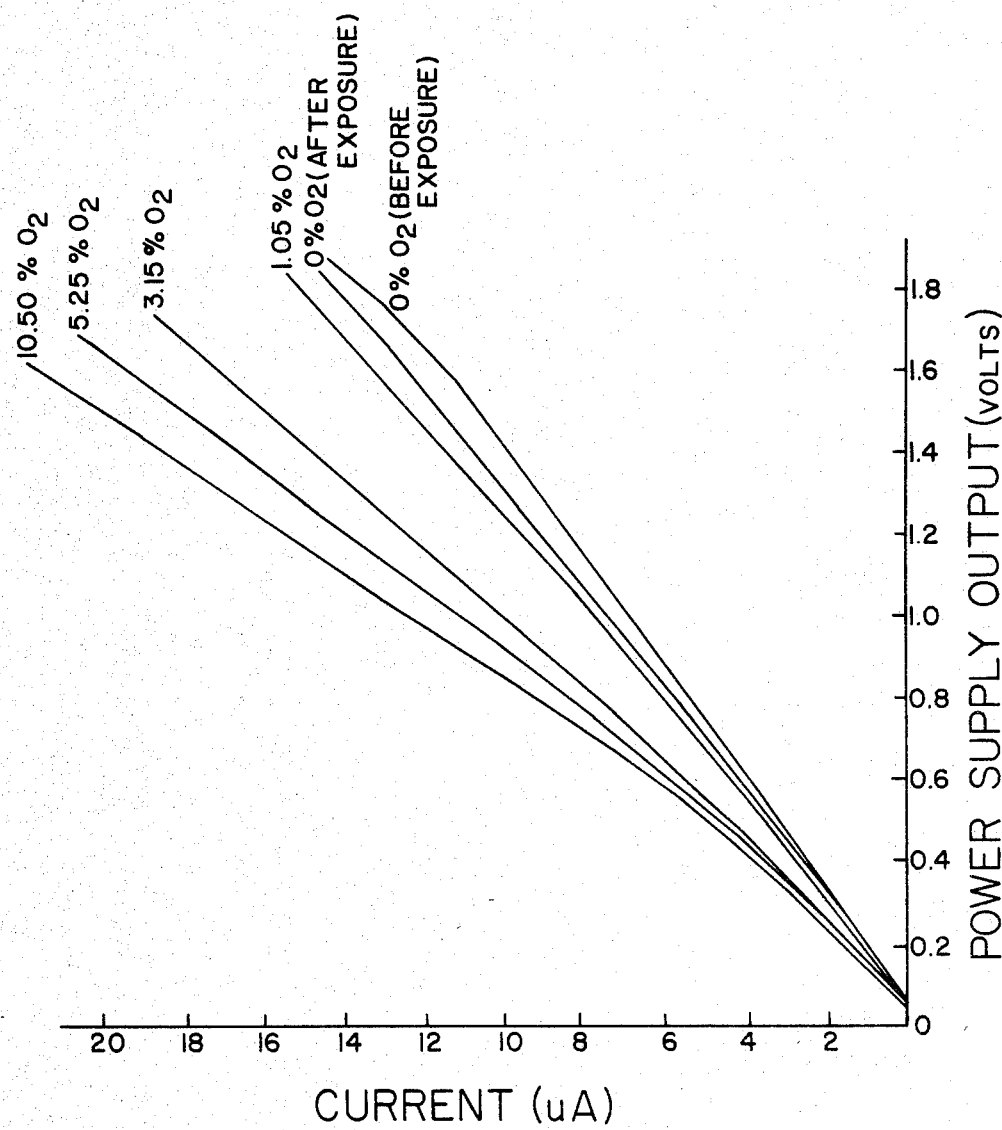
FIG. 2 is a set of IV curves for the sensor of example 1 at various oxygen gas concentrations.

The potential across the two electrodes was scanned over the range of 0 to approximately 1.9 V using a Sorensen model QRD 20-4 power supply which was driven by a Wavetek model 166 function generator. The function generator was set such that with each manual triggering, a ramp output was obtained (0 to approximately 1.9 V) with very fast decay time. The sweep rate was adjusted to 46 mV/sec. A 5K ohm precision resistor in series with the anode was used to monitor the current flow (potential drop across the resistor). The IV curves (FIG. 2) were recorded using a Gould model 3054 X-4 recorder with the X amplifier connected to the power supply and the Y amplifier connected across the 5K ohm resistor. From the results in FIG. 2, it can be seen that the sensor responds to changes in oxygen concentration. In this example, however, the response is not very linear and the signal does not return to the original baseline. These two problems are attributed to poisoning of the large Pt cathode with $OH^-$ (from the $O_2$ reduction) which cannot be diffused away fast enough in this configuration.

The smaller Pt electrode ($2 \times 23$ mm) was not used in this experiment.

EXAMPLE 2

This example shows how to print multiple electrodes on a single substrate. It also shows a configuration that exhibits a very linear response to $O_2$ conc. with low hysteresis with decreasing $O_2$ conc. A total of six electrodes were printed on a single alumina substrate ($1'' \times 1''$, approximately 0.5 mm thick). Three of the electrodes were gold (Au) and three were silver (Ag). Each gold electrode is followed by a silver electrode, such that we have a total of three sensors on the substrate. The gold ink was from Electroscience Laboratories, Inc. (#8835-1B) while the silver ink was the same as in Example 1. The gold electrodes were printed first due to the higher firing temperature needed following the ink manufacturer's instructions. After printing the Ag electrodes, as in Example 1, the ceramic insulation was deposited such that the following electrode areas were exposed Ag-24.2 mm$^2$, Au-2.3 mm$^2$ (total for each cathode and for each anode). Masks were developed and used for fabrication of these electrodes, as in Example 1, such that the exposed surfaces (those used for polarography) are reproducible and well-defined.

Chloridation of the exposed Ag electrode was done as in Example 1 using a 1.1% NaCl solution with the last anodization step being 11 minutes (at approximately 5mA/cm$^2$) instead of 10 minutes (at approximately 5.6 mA/cm$^2$) as in Example 1. P-HEMA membranes were cast over the required area as in Example 1. Insulated wires (28 AWG) were soldered on the contact points using regular Kester "44" solder. Epoxy was also applied over the contact points, as in Example 1.

Figure 3:
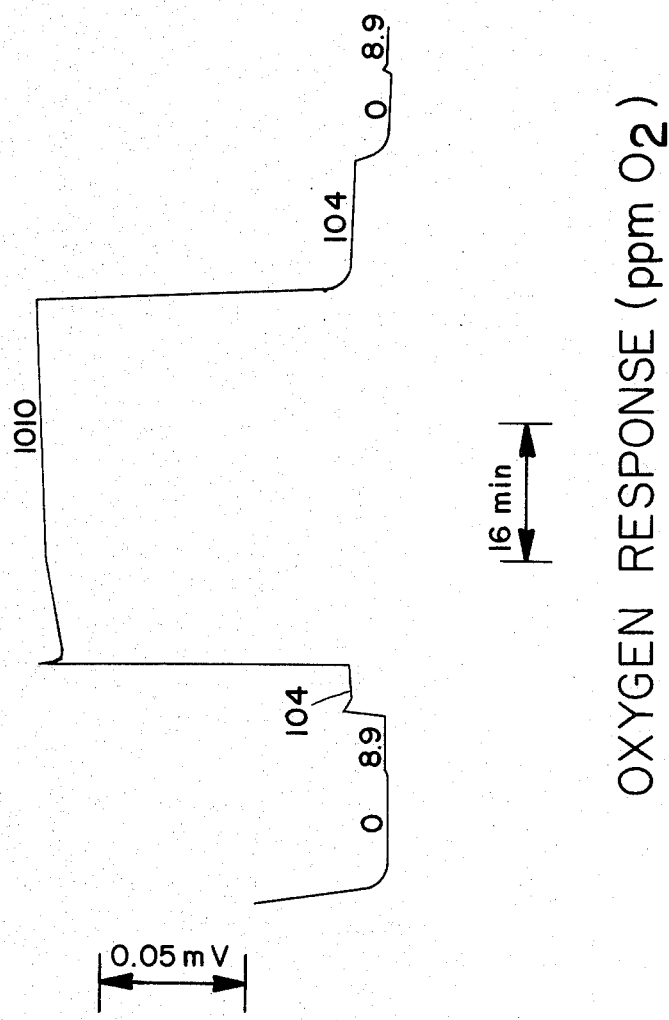
FIG. 3 shows oxygen response and the very low hysteresis of the sensor of example 2.

After immersion in unbuffered saline (approximately 0.1 M NaCl) overnight, the 3-sensor containing chip was mounted in the flow cell described in Example 1 and tested. First, linear sweep voltametery experiments were performed (as in Example 1). Then one at a time the three sensors were polarized utilizing a Sorensen model QRD 20-4 power supply set at 1.230 V. The Au cathode of each sensor was connected to the negative output of the power supply while the Ag/AgCl anode of each sensor was connected to the positive output through a 1K ohm resistor in series. The current flow through the 1K ohm resistor (potential drop across the resistor) was monitored continuously with a Gould strip chart recorder (model 110). This recorder was set at a very sensitive scale with the 1 second signal filter switched on. Representative data of various ppm levels of oxygen detected using one of the three sensors is shown in FIG. 3. The response of each of the sensors, of this design, was found to be very linear and fast, while the hysteresis in decreasing $O_2$ concentrations is reasonably small (again see FIG. 3 for example). For this experiment precision gas mixtures of $O_2$ and $N_2$ supplied by Air Products were used.

EXAMPLE 3

Three sensors fabricated according to the process described in Example 2 were separated by cutting the ceramic substrate with a diamond wafering saw (Buehler, Isomet-blade No. 11-4255), just before the membrane casting step.

In this example these sensors are compared with the HP oximeter model 47201A oxygen saturation analyzer also described in this example. In each figure line A is the response of the HP oximeter and line B is the response of the sensor of the present invention.

Membranes were cast over each individual sensor by dip coating in a 10% p-HEMA solution in methanol (p-HEMA from Chemalog, Cat. No. 74-6490-00). After the dipping step, each sensor was held flat for approximately 30 seconds, long enough for the solvent to evaporate and form a reasonably uniform polymeric film over the area of interest.

Contact wires and epoxy were applied as in Example 2 and the sensors were immersed in saline overnight as in Example 2.

After overnight immersion in the saline solution one of the sensors was mounted on the fingertip (middle finger of left hand) of a male volunteer (with band-aids, and silicon adhesive from Dow Corning) and polarized for $O_2$ monitoring at 1.17 V, using the equipment described above in Example 2 for polarization potential and current monitoring. The sensor was allowed to equilibrate at the physiological skin temperature (no heating was employed).

An HP oximeter model 47201A (Hewlett-Packard) was used for comparative measurement and its probe (thermostated at 44°±0.5° C.) was mounted on the ear of the volunteer. When the blood oxygen partial pressure (PO$_2$) of the volunteer was changed (by hyperventilation), we observed a qualitative correlation between the two devices (HP oximeter and the polarographic sensor of the present invention).

Figure 4:
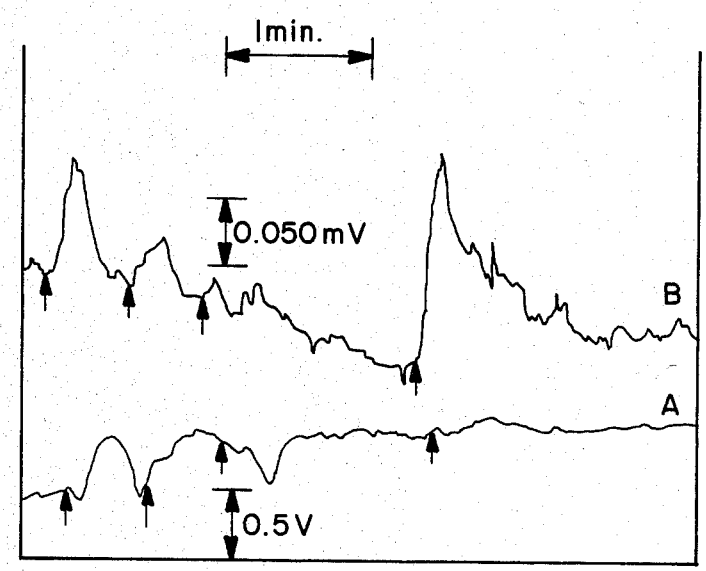
FIGS. 4 and 5 are simultaneous graphs of the response of sensors of the present invention.
Figure 5:
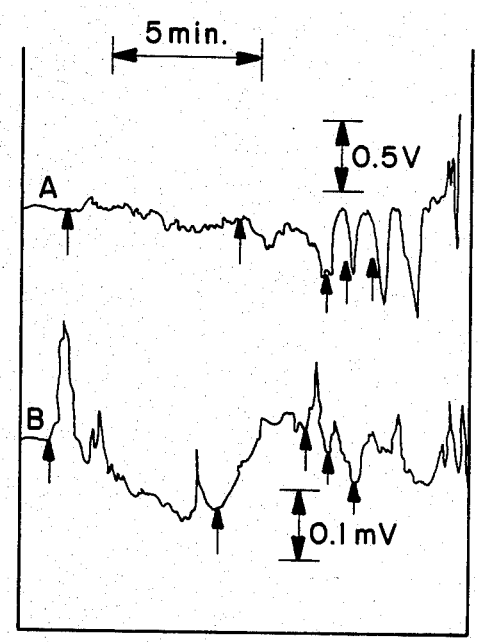

Some of the recorded data is shown in FIGS. 4 and 5.

In both FIG. 4 and 5 the arrows indicate the points at which hyperventilation was started on the volunteer. In both Figures line A is the response of the HP oximeter and line B is the response of the sensor of this example. Note that the sensor of the present invention responds better in all cases. This better response was realized without heating the volunteers skin while the HP oximeter required heating to 44°±0.5° C.

This experiment has demonstrated that a PO$_2$ sensor fabricated according to the procedure described above, responds well (faster than the oximeter) to the blood PO$_2$ diffused through the human skin and without the need for an auxiliary heating means.

What is claimed is:

1. A solid state transcutaneous oxygen sensor comprising:
   (a) an electrically insulating substrate;
   (b) a first electrode comprising a noble metal on said substrate of (a);
   (c) a second electrode comprising a silver/silver halide reference electrode on said substrate of (a);
   (d) an insulating dielectric layer on said components (a), (b) and (c) characterized in that at least a portion of component (b) and component (c) remains exposed; and
   (e) an oxygen permeable polymeric membrane containing a bound liquid electrolyte over at least said exposed portion of said first and said second electrodes;
   (f) a polymeric oxygen permeable, liquid impermeable, biocompatible membrane coating over said oxygen permeable polymeric membrane containing a bound liquid electrolyte;
   further characterized in that said exposed portions of said first and second electrodes have well-defined surface areas.

2. A solid state oxygen sensor as claimed in claim 2 wherein said second electrode is selected from the group consisting of silver/silver chloride, silver/silver bromide, silver/silver fluoride, and silver/silver iodide.

3. A solid state oxygen sensor as claimed in claim 2 wherein said second electrode is composed of silver/silver chloride.

4. A solid state oxygen sensor as claimed in claim 2 wherein said oxygen permeable membrane, component (e), is selected from the group consisting essentially of hydrogels and hydrophilic polymers.

5. A solid state oxygen sensor as claimed in claim 4 wherein said hydrogel is selected from the group consisting of homopolymers and copolymers of N-vinyl pyrrolidone, glycidyl methacrylate and hydroxyethyl methacrylate (HEMA).

6. A solid state oxygen sensor as claimed in claim 2 wherein said component (f) is selected from the group consisting of TEFLON, polyphenylene oxide, polyethylene and polypropylene.

7. A solid state oxygen sensor as claimed in claim 2 wherein said electrically insulating substrate is selected from the group consisting of ceramic chips, ceramic wafers, ceramic plates, glass chips, glass wafers and glass plates.

8. A solid state oxygen sensor as claimed in claim 2 wherein said electrically insulating substrate is alumina.

9. A solid state oxygen sensor as claimed in claim 2 wherein said oxygen permeable polymeric membrane bound liquid electrolyte is an alkali metal halide in a solvent.

10. A solid state oxygen sensor as claimed in claim 9 wherein said alkali metal halide is NaCl, KCl or mixtures thereof.

11. A solid state oxygen sensor as claimed in claim 9 wherein said liquid electrolyte is a 0.09 N isotonic saline solution.

12. A solid state oxygen sensor as claimed in claim 9 wherein said solvent is selected from the group consisting of water, ethylene glycol and mixtures thereof.

13. A solid state oxygen sensor as claimed in claim 9 wherein said liquid electrolyte comprises 0.1 molar NaCl in a solvent comprising a 1:1 ratio, by weight, water and ethylene glycol.

14. A solid state oxygen sensor as claimed in claim 2 wherein said noble metal of component (b) is selected from the group consisting of gold, silver, palladium, iridium, rhodium, ruthenium, osmium, platinum and alloys thereof.

15. A method for non-invasively measuring the blood oxygen partial pressure (PO$_2$) of a patient, which method comprises applying a polarization potential to a solid state transcutaneous oxygen sensor comprising:
   (a) an electrically insulating substrate;
   (b) a first electrode comprising a noble metal on said substrate of (a);
   (c) a second electrode comprising a silver/silver halide reference electrode on said substrate of (a);
   (d) an insulating dielectric layer on said components (a), (b) and (c) characterized in that at least a portion of component (b) and component (c) remains exposed;
   (e) an oxygen permeable polymeric membrane containing a bound liquid electrolyte over at least said exposed portion of said first and said second electrodes;
   (f) a polymeric oxygen permeable, liquid impermeable, bicompatible membrane coating over said oxygen permeable polymeric membrane containing a bound liquid electrolyte; and
   (g) further characterized in that said exposed portions of said first and second electrodes have well-defined surface areas;
then contacting the patient's skin with the sensor and measuring the current flow response.

* * * * *

UNITED STATES PATENT AND TRADEMARK OFFICE
CERTIFICATE OF CORRECTION

PATENT NO. : 4,534,356
DATED : August 13, 1985
INVENTOR(S) : Nicholas Papadakis

It is certified that error appears in the above-identified patent and that said Letters Patent are hereby corrected as shown below:

In column 9, lines 31, 38, 47 and 51 and in column 10, lines 3, 5 and 23, the claim reference numeral "2", each occurence, should read --1--.

Signed and Sealed this

Twelfth Day of November 1985

[SEAL]

Attest:

Attesting Officer

DONALD J. QUIGG

Commissioner of Patents and Trademarks